United States Patent [19]

Shaw et al.

[11] Patent Number: 5,043,143

[45] Date of Patent: Aug. 27, 1991

[54] ANALYZER HAVING HUMIDITY CONTROL APPARATUS

[75] Inventors: James D. Shaw, Hilton; Martin F. Muszak, Rochester, both of N.Y.

[73] Assignee: Eastman Kodak Company, Rochester, N.Y.

[21] Appl. No.: 500,815

[22] Filed: Mar. 28, 1990

[51] Int. Cl.$^5$ .................. G01N 33/00; G01N 35/02; G01N 35/04; G05D 22/00

[52] U.S. Cl. .................................... 422/65; 422/64; 422/63; 422/67; 422/104; 436/46; 436/55; 236/44 A; 236/44 B; 236/44 C; 236/44 R

[58] Field of Search ............... 422/62, 63, 64, 65, 422/67, 100, 102, 104, 82.05; 436/46, 55, 809; 236/44 A, 44 B, 44 C, 44 R, DIG. 13; 165/21; 219/362, 400, 401, 439, 440

[56] References Cited

U.S. PATENT DOCUMENTS

| Re. 30,730 | 10/1981 | Duff | 422/64 |
|---|---|---|---|
| 3,616,264 | 10/1971 | Ray et al. | 195/127 |
| 3,825,723 | 7/1974 | Roeser | 219/401 |
| 3,930,612 | 1/1976 | Brakebill et al. | 236/44 R |
| 4,298,570 | 11/1981 | Lillig et al. | 422/65 |
| 4,512,952 | 4/1985 | Blanding et al. | 422/63 |
| 4,659,009 | 4/1987 | Newell, III | 236/44 C |
| 4,676,951 | 6/1987 | Armes et al. | 422/65 |
| 4,708,886 | 11/1987 | Nelson | 422/63 |
| 4,711,294 | 12/1987 | Jacobs et al. | 236/44 R |
| 4,750,545 | 6/1988 | Hile et al. | 236/44 B |
| 4,876,204 | 10/1989 | Inoue et al. | 422/63 |

FOREIGN PATENT DOCUMENTS

| 0299519 | 1/1989 | European Pat. Off. | |
|---|---|---|---|
| 2030962 | 1/1985 | Japan | |
| 0013162 | 1/1986 | Japan | 422/82.05 |
| 0173034 | 8/1986 | Japan | 165/21 |
| 0180113 | 7/1988 | Japan | 236/44 R |
| 0080866 | 3/1989 | Japan | 422/82.05 |
| 2140912 | 12/1984 | United Kingdom | 236/44 A |

Primary Examiner—David L. Lacey
Assistant Examiner—Kimberly A. Trautman
Attorney, Agent, or Firm—Dana M. Schmidt

[57] ABSTRACT

There is described an analyzer for determining analytes of a body liquid, in which stacks of test elements are stored prior to use. To control the level of humidity in which the stacks are stored, first and second compartments are provided with access openings connecting them to the stack-storage area. A mechanism is provided for selectively closing off and opening up the access openings, and for actively forcing air to flow from either of the compartments into the storage area. One of the compartments has a supply of water, and the other has a desiccant.

7 Claims, 6 Drawing Sheets 5,043,143

ANALYZER HAVING HUMIDITY CONTROL APPARATUS

FIELD OF THE INVENTION

This invention relates to storage and supply means used to provide test elements to an analyzer, particularly analyzers that use dried test elements.

BACKGROUND OF THE INVENTION

Conventional analyzers have been constructed to provide some level of climate control in parts thereof. The most frequent climate control is temperature control provided in the incubator, that is, in the portion where test samples are reacting with reagents prior to a reading being made at a detecting station. Such temperature control can include means for blowing air over the samples and over heating elements, as shown, for example, in U.S. Pat. Re. 30,730 and U.S. Pat. No. 3,616,264.

It has also been known that climate control is equally important in the storage area or supplying means of test elements, particularly when so-called "dried" slide like test elements are used. For example, analyzers have been known to provide a desiccant inside a cartridge, adjacent a plurality of such test elements while stored, as in Japanese Kokai No. 62/030962. However, this is not acceptable in analyzers having a large storage area for test elements prior to sample addition. That is, some of the other test elements may require moistening air, which would be deleterious to such desiccants. For example, test elements for the assays of total protein, magnesium, albumin and calcium need a high relative humidity of about 33%, whereas those for the assays of LDH, CK, AST and gamma glutamyltransferase need only 15%.

Yet another approach, currently used in analyzers available under the trademark "Ektachem 700" analyzers from Eastman Kodak Company, is to provide two separate storage areas of cartridges. In one area, those that prefer to be stored under dry conditions have a desiccant stored with them. This is the only humidity control, that is, it removes moisture only, and does so passively. In the other storage area, cartridges are placed that prefer a higher degree of relative humidity, and a salt pad capable of adding or removing moisture within a range is present. In this other area, the addition of moisture is passive only—there is no attempt to make the air in the storage area more uniform in content.

Although such a system has provided control of the relative humidity, there have been instances in which better and more rapid control was needed. For example, test elements and cartridges stored with only a desiccant present can become too dry when used in, e.g., desert conditions. The problem with the storage atmosphere being too dry is that it induces reduced storage life.

Thus, it has been discovered that conditions can be experienced in which both water addition and deletion are required, alternately, to the atmosphere of the storage area, over a period of time. Merely storing a drying means or a wetting means in a cartridge or its storage area does not permit a rapid opposite change in the relative humidity in such a cartridge, particularly when such means are passive only, as defined herein.

Accordingly, it has been a problem prior to this invention that the storage area or supplying means for slide like test elements has not been able to provide the proper relative humidity for storage that each kind of test element needs. A further problem is that control of such relative humidity has been cumbersome.

SUMMARY OF THE INVENTION

We have constructed an analyzer in which the slide like test element supplying means can be easily maintained, while stored prior to use, at the proper level of relative humidity, even when the test elements are stored and/or used under extreme conditions.

More specifically, there is provided an analyzer for analyzing body liquids to determine concentration levels of analytes, the analyzer including means for supplying test elements for a variety of different assays, means for incubating a test element after a body liquid is deposited onto a test element taken from the supplying means, means for transferring a test element from the supplying means to the incubating means, and means for controlling the relative humidity of at least some of the test element supply means. The analyzer is improved in that the humidity controlling means comprise a first compartment having exposed water therein, a second compartment having a desiccant therein, the compartments each having an access opening for air communication with each of the supplying means, door means for separately closing off and opening up each of the access openings, control means for operating the door means in response to the relative humidity present at the supplying means, and means for actively forcing air to travel from the access openings to the supplying means, and further including means associated with the supplying means for sensing the relative humidity.

Accordingly, it is an advantageous feature of the invention that an analyzer is provided that provides positive water addition and/or water deletion to the atmosphere in the portion that stores and supplies test elements for use, as needed.

Other advantageous features will become apparent upon reference to the following description of the preferred embodiments, when read in light of the attached drawings.

DESCRIPTION OF THE PREFERRED EMBODIMENTS

The invention is hereinafter described with respect to a preferred type of a) storage and supply means for elements, b) test elements and cartridges, and c) transfer means, incubator, and detector station. In addition, it is useful for other kinds of storage and supply stations, other kinds of test elements and cartridges, and other kinds of transfer means, incubator and detector stations.

The invention is based on the determination that both water addition means and water deletion means should be supplied, to all stacks of test elements stored in the analyzer, in an alternative fashion, and not as a source within each cartridge individually, but rather to the supply means that house the cartridges. Furthermore, the air is to be actively forced to flow and travel from the means for adding or deleting moisture, to the stacks of elements. As used herein, "active" humidity control distinguishes from "passive" humidity control in that in the former, air is positively forced to travel between the humidity control and the stacks of elements. In the latter "passive" system, there is simply a humidity control means somewhere "in the box", and the user hopes that its influence is adequate over elements present even at far distant reaches.

Figure 1:
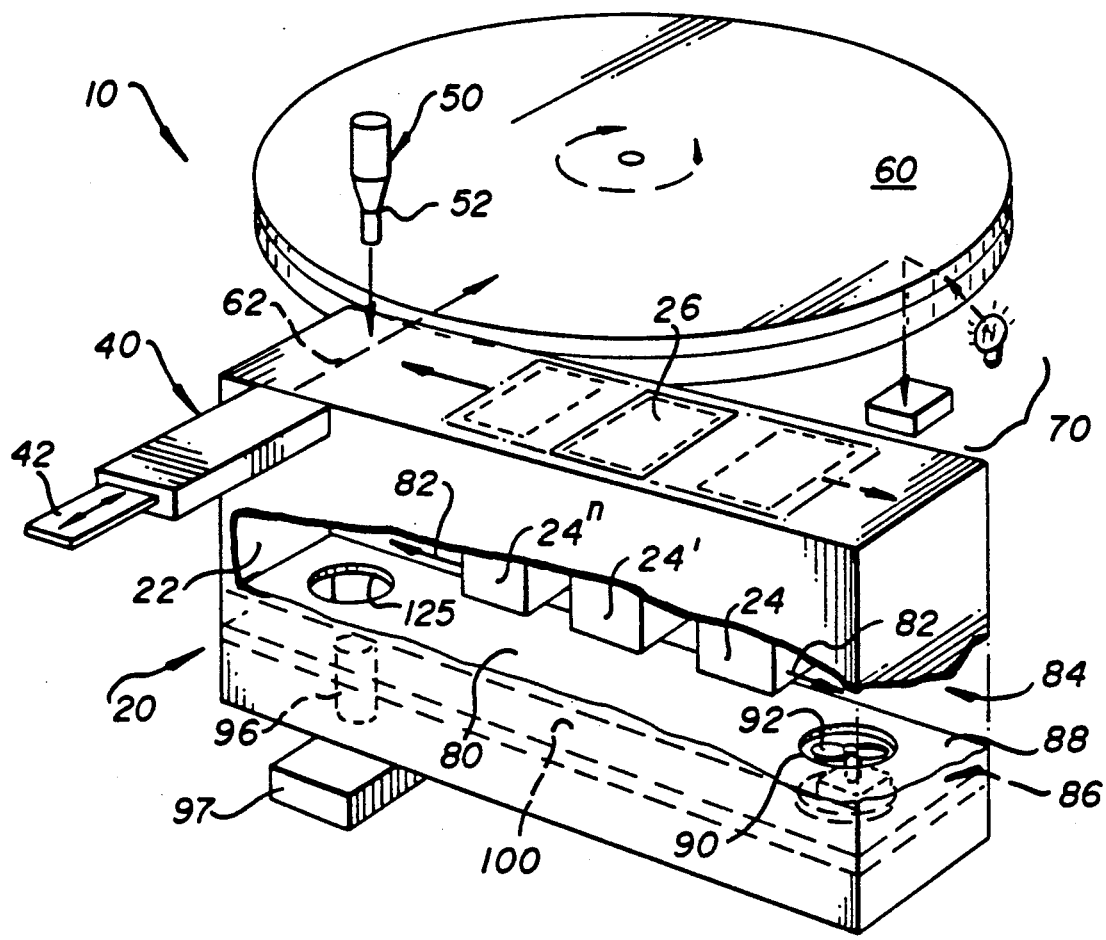
FIG. 1 is a perspective, partially schematic view of a [simplified] analyzer constructed in accord with the invention.

Thus, FIG. 1, an analyzer 10 constructed in accordance with the invention comprises, as is conventional, a test element storage and supply station 20, a test element transfer means 40, means 50 for dispensing a body liquid onto a test element removed from station 20 by transfer means 40, an incubator 60 for incubating a test element containing body liquid so dispensed, and a detector station 70 such as a reflectometer, for detecting changes in the test elements after incubation, preferably while still in the incubator. The storage and supply station 20 preferably comprises a housing 22 having walls that completely enclose a plurality of stacks of test elements E, FIG. 2, each stack being preferably enclosed in a movable cartridge 24, 24', etc., up to $24^n$ for $n+1$ cartridges and $n+1$ stacks, all of which is conventional. (Only three are shown in FIG. 1 for purposes of illustration). Any suitable means can be provided for inserting and removing cartridges, such as door 26.

Each cartridge is preferably limited to generally identical test elements for a single assay, so that different assays are provided by different cartridges. The cartridges and assays are preferably of the type available under the trademark "Ektachem" cartridges to "Ektachem" slides, respectively, from Eastman Kodak Company.

Figure 4:
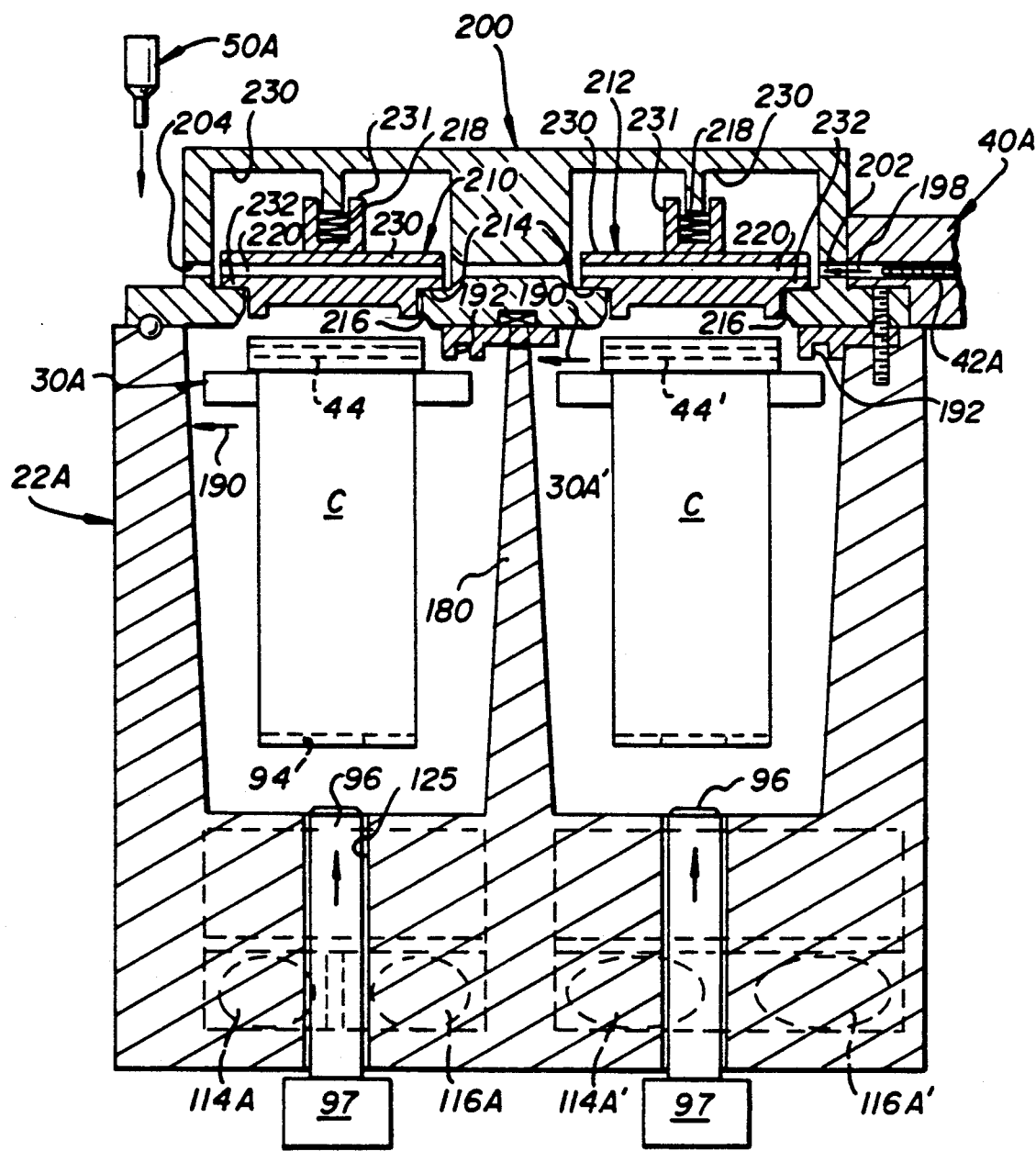

Regarding transfer means 40, preferably such means utilizes a pusher blade 42 that is insertable into the top of a cartridge through a slot 44, FIG. 4. Regarding dispensing means 50, preferably it uses a disposable tip 52, FIG. 1, and automated means (not shown) for aspirating several aliquots of a sample of body liquid into tip 52, and then dispensing an aliquot at a time. Incubator 60 is preferably a rotating incubator with a plurality of stations around the circumference for holding a test element inserted after treatment by dispensing means 50, by blade 42 as indicated by arrow 62. Useful examples of such transfer means, liquid dispensing means, incubator and detector station include, but are not limited to, those provided by analyzers available under the trademark "Ektachem" analyzers from Eastman Kodak Company.

Figure 2:
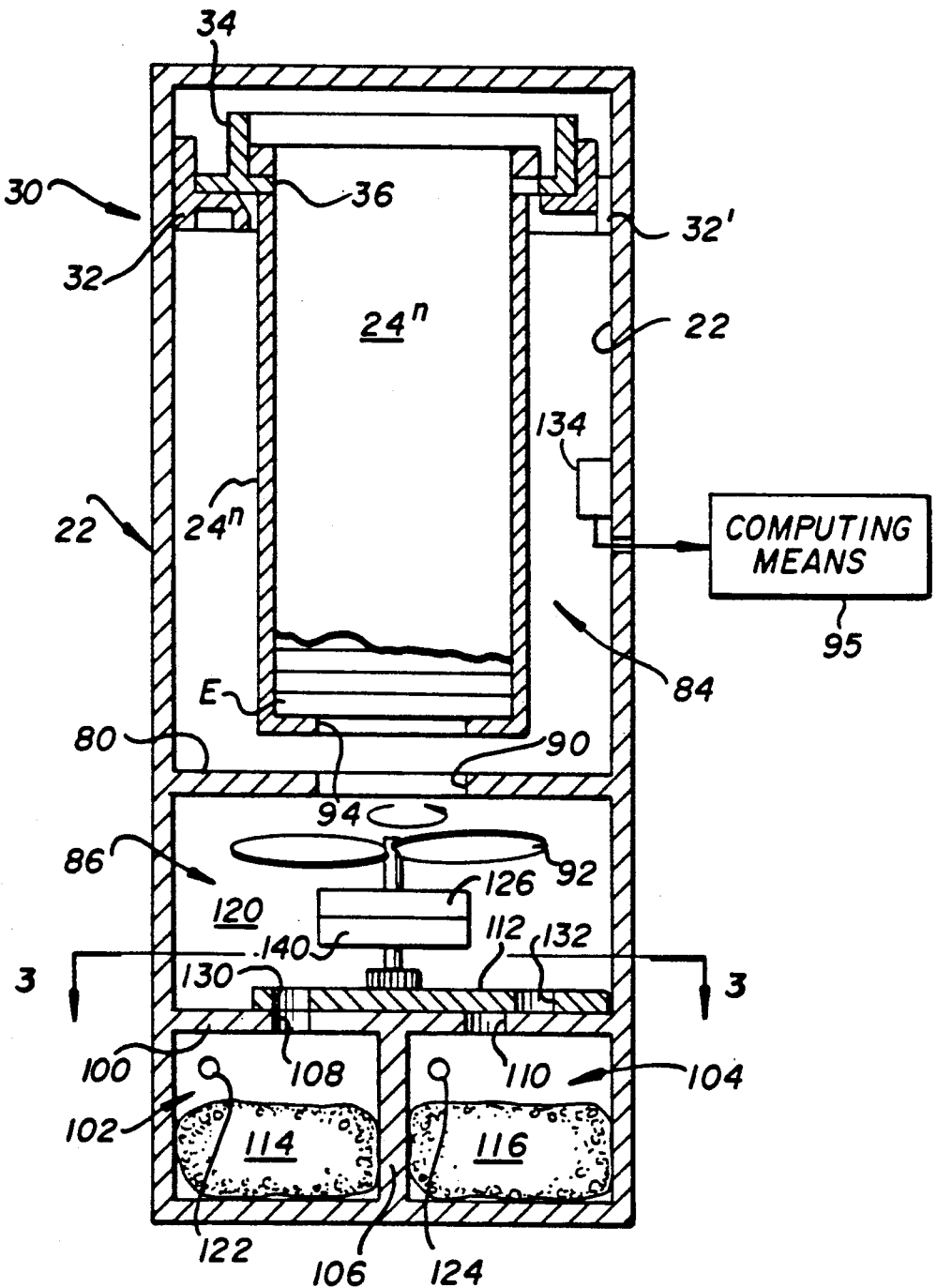
FIG. 2 is an elevational view in section of the test element storage and supplying means, taken through the end holding the water and desiccant containers.

All parts of the analyzer are preferably controlled by computing means 95, FIG. 2, and related input and output devices such as a keyboard and CRT display, not shown, all of which are conventional.

Concerning storage and supply station 20 in particular, this station can have any configuration, a linear one being illustrative. In such a case, FIG. 2, a track 30 can be provided, which comprises opposed rails 32 and 32'. On these rails, a carrier 34 reciprocates, preferably as driven by a motor, not shown. Carrier 34 includes cut out portions or apertures 36 that mate with and support a cartridge $24^n$. Alternatively, housing 22 can be arcuate, not shown, and track 30 can be an annular ring or portion thereof that rotates about point P. It is the environment within housing 22 and cartridges 24, 24'...$24^n$ that the relative humidity is to be controlled.

In accord with the invention, means are included in housing 22 for adding or deleting water to this atmosphere, preferably in a mutually exclusive manner. More specifically, a wall 80 extends horizontally across the bottom of station 20, preferably just under the path of movement, arrows 82, FIG. 1, of the cartridges, to separate housing 22 into an upper compartment 84 and a lower one 86. Near one end 88 of wall 80, an access opening 90 is provided. Under opening 90, fan 92 is disposed, FIGS. 1 and 2, to force air to flow or travel through opening 90 and into upper compartment 84 and the cartridges $24^n$. (Each cartridge includes a lower aperture 94, FIG. 2, that allows the insertion of a rod 96, FIGS. 1 and 4, operated by a motor 97 to raise the stack of test elements up into position to engage blade 42, as is conventional.)

To allow the fan to force drier, or wetter air into compartment 84, compartment 86 is further subdivided by wall 100 to form two enclosed subcompartments 102 and 104, as better noted in FIG. 2. A separating wall 106 is positioned between them, and access openings 108 and 110 are provided in wall 100 for each of the subcompartments. A door 112 is provided for each of openings 108 and 110. Subcompartment 102 contains either means for adding moisture to the air or means for removing moisture, while the other one contains the other. For example, subcompartment 102 can contain a sponge 114 saturated with water, whereas subcompartment 104 contains in that case a desiccant 116. Alternatively, not shown, sponge 114 can be replaced by a misting device that turns on a fine mist when opening 108 is uncovered.

Figure 3:
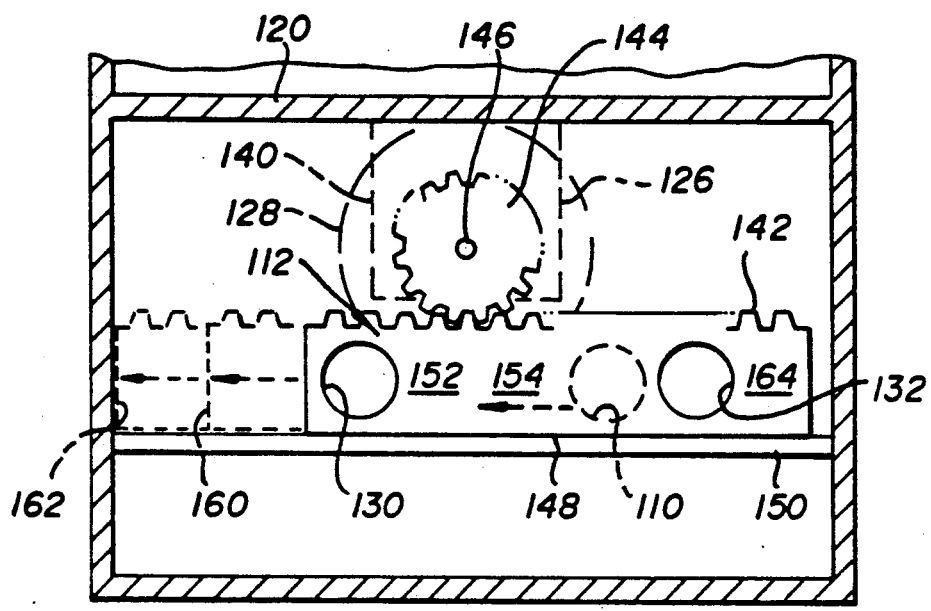
FIG. 3 is a plan section view taken generally along the line III—III of FIG. 2.

Both subcompartments 102 and 104, as well as compartment 86, preferably have an endwall 120 that completes their enclosure, FIGS. 2 and 3. However, endwall 120 includes air return openings 122, 124 only at subcompartments 102 and 104, FIG. 2, that cooperates with air return aperture 125 in wall 80, FIGS. 1 and 4, to allow air to recirculate.

To drive fan 92, a motor 126 is provided, (shown in phantom, FIG. 3) preferably mounted on wall 120. The rotation 128 of the blade of fan 92 clears this wall.

Door 112 requires openings 130, 132 to cooperate with openings 108 and 110, respectively, FIG. 2. These are positioned so that either opening 130 is aligned with opening 108 while opening 132 is not aligned with opening 110, as shown, or vice versa.

Door 112 is operated so as to add moisture, or remove it, as is dictated by at least one humidity sensor 134 positioned within compartment 84. The response of the sensor is received by computing means 95, which in turn operates fan 92 and the door 112 as follows:

To control the movement of door 112 and thus the change in alignment of openings 130 and 132, door 112 preferably is driven by a single motor 140, FIG. 2, preferably mounted on wall 120. Any connection between motor 140 and door 112 is useful. For example, a rack and pinion connection is provided when edge 142 of door 112 is a rack and a pinion gear 144 is mounted on drive shaft 146 of motor 140, FIG. 3. Opposite edge 148 of door 112 slides on shoulder 150. In this fashion, access to both subcompartments is controlled by a single motor.

To ensure that motor 140 provides that either opening 108 is solely accessible, or opening 110 is solely accessible, or neither opening is accessible, openings 130 and 132 are positioned, FIG. 3, so that solid portions 152 and 154 of door 112 remain available to cover opening 108 as the door moves first to the left to first phantom position 160, and then to the second phantom position 162. Similarly, solid portion 164 is positioned to the right of opening 132 to allow the door to cover opening 110 when the opposite end is in the phantom position 162.

Because fan 92 is not constantly on, an auxiliary fan (not shown) can be used to recirculate air in compartment 84.

More than one track can be provided as a source of cartridges, FIG. 4. In this embodiment, one track is selected for cartridges requiring generally a first relative humidity level, and the other for those requiring a different relative humidity level, so that each track has its own set of water addition means and water deletion means. Parts similar to those previously described bear the same reference numeral, to which the distinguishing suffix A is appended.

Thus, a housing 22A is provided for storage and supply of test elements from cartridges C, for transfer via blade 42A in means 40A to a dispensing station using dispensing probe 50A. However, in this case, there are two tracks 30A and 30'A, side by side, separated by a common housing wall 180. They can be linear as shown, or any other shape, for example, that of annular rings. The tracks are shown generically, as they can be configured in any convenient form including that shown in FIG. 2. Alternatively, each track can be radially separable, arrow 190, to allow a used cartridge C to fall through housing 22 and out a trap door, not shown, in the bottom of housing 22A. Preferably, tracks 30A and 30'A cooperate with sensors 192 to indicate which cartridge is where.

As in the previous embodiment, each track 30A and 30'A has its own set of water adding means 114A and water deleting means 116A, or means 114'A and deleting means 116'A, respectively, shown in phantom FIG. 4. The door operating means providing access to 114A or 116A, or 114'A or 116'A, are constructed similarly to that of the embodiment of FIGS. 2 and 3. That is, there is a separate door and motor (not shown) for each of the two tracks. By this construction, the relative humidity for, e.g., track 30A and its cartridges can be maintained at a higher level than that of track 30'A and its cartridges.

Because pusher blade 42A necessarily passes over both track 30A and 30'A on track 198, and a cartridge of each track necessarily intersects the blade path 198, it is desirable that a seal be maintained at the top, in conjunction with the blade passage, to ensure that there is minimal air mixing between the two tracks. A preferred embodiment to achieve these results is as follows:

The top portion 200 of housing 22A accommodates the passage of blade 42A and a test element dealt off the top of a stack from track 30A or 30'A. More specifically, top portion 200 has a blade entrance port 202 and an exit port 204 fixed in the housing, and floating members 210, 212. The floating members are displacably seated on annular valve seats 214 disposed around an opening 216 that will allow a cartridge to be raised up into the path 198 to be engaged at groove 44 by blade 42A. Members 210 and 212 are each biased downwardly against seats 214 by a compression spring 218.

Because each member 210 or 212 serves as a substitute blade guide if its cartridge is not raised up, a groove 220 horizontally extends through the member. Because each member is pushed up out of blade path 198 if its cartridge is raised up, a space 230 is formed in portion 200 to accommodate member 210 or 212 when spring 218 is compressed. (Movement upward of a stack of elements by rod 96 also causes cartridge C to be raised up against member 210 or 212).

Although not essential, member 210 or 212 can be constructed so that top portion 230 thereof, from which boss 231 extends to receive spring 218, can be easily removed from bottom portion 232 (not shown), whereby any test element jams can be readily fixed.

Figure 5:
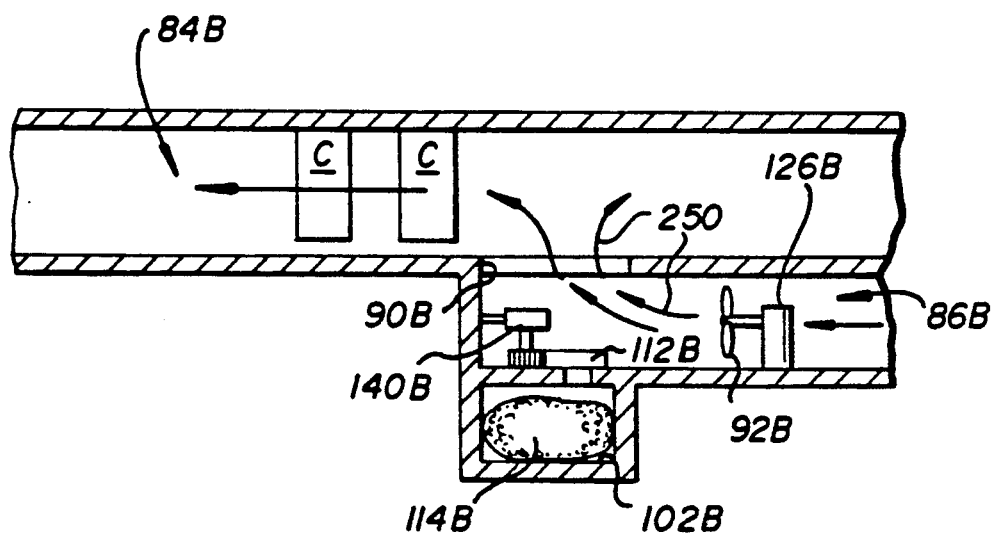
FIGS. 4-5 are elevational views in section illustrating alternate embodiments.

The fan for positive air displacement need not be vertically disposed. Instead, it can be mounted to force air to flow first horizontally and then vertically, FIG. 5. Parts similar to those previously described bear the same reference numeral to which the distinguishing suffix B is appended.

Thus, housing 22B has an upper compartment 84B and a lower compartment 86B as before, with an access opening 90B connecting the two. Cartridges C are moved along a track in compartment 84B, as with the previous embodiments, and two subcompartments, of which only subcompartment 102B is shown, provide either water adding means or water deleting means, such as water filled sponge 114B. A door 112B is operated by a motor 140B as described previously.

However, unlike the previous embodiments, fan 92B is disposed to blow air first horizontally through lower compartment 86B, by its motor 126B, arrow 250.

Figure 6:
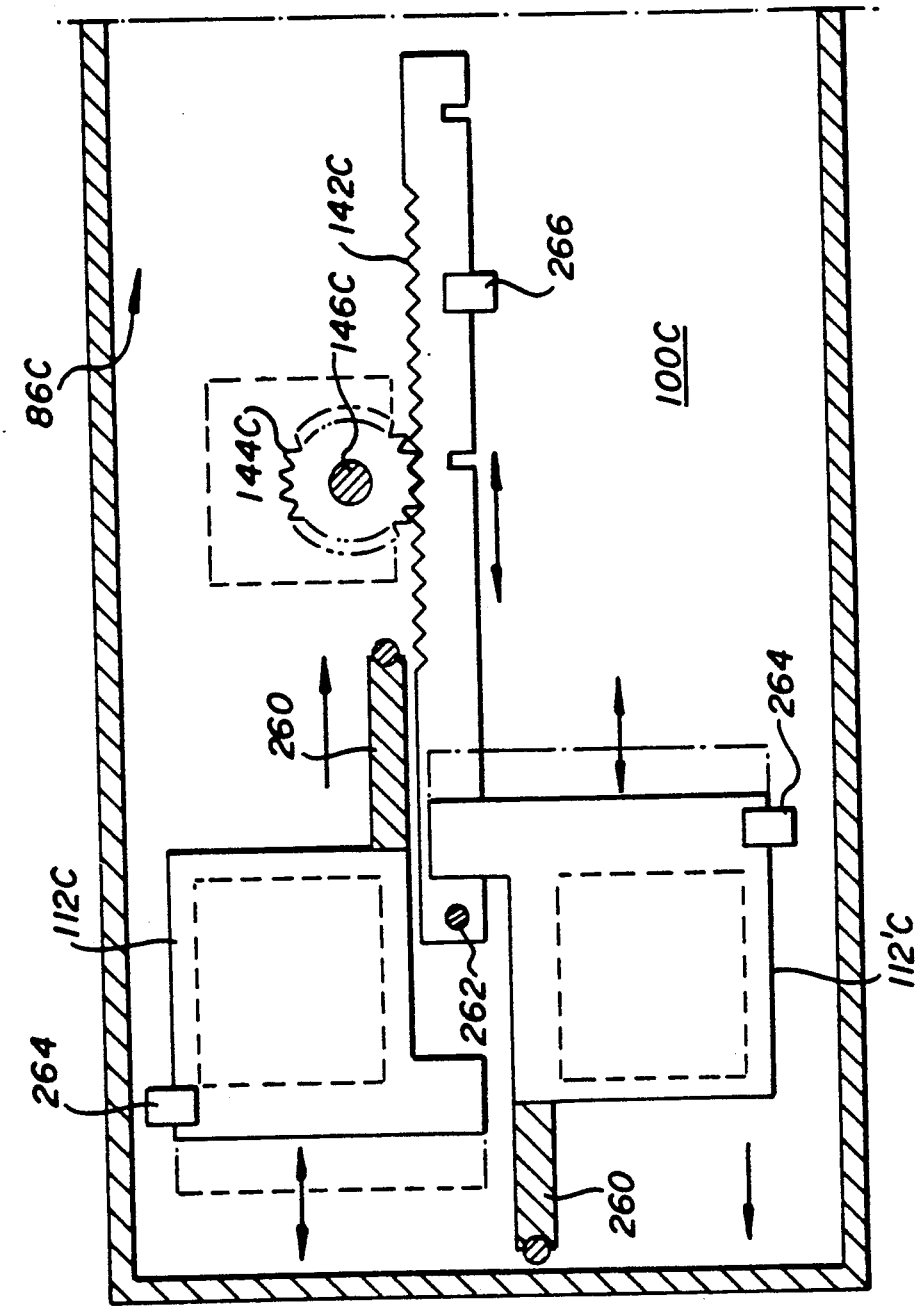
FIG. 6 is a plan section view similar to FIG. 3, but of yet another alternate embodiment.

It is not necessary that a single door be used for both access openings from the subcompartment, FIG. 6. Parts similar to those previously described bear the same reference numeral, to which the distinguishing suffix "C" is appended. Thus, wall 100C that separates compartment 86C from the subcompartments has a rack 142C and pinion gear 144C operated by drive shaft 146C, to open doors 112C and 112'C over the access openings, as before. However, door 112C is separate from door 112'C, each being biased by a tension spring 260 into a closed position. A post 262 on one end of rack 142C either pushes door 112C open, or pulls door 112'C open, alternatively. Sensors 264 and 266 sense the door positions and the rack positions, respectively.

Figure 7:
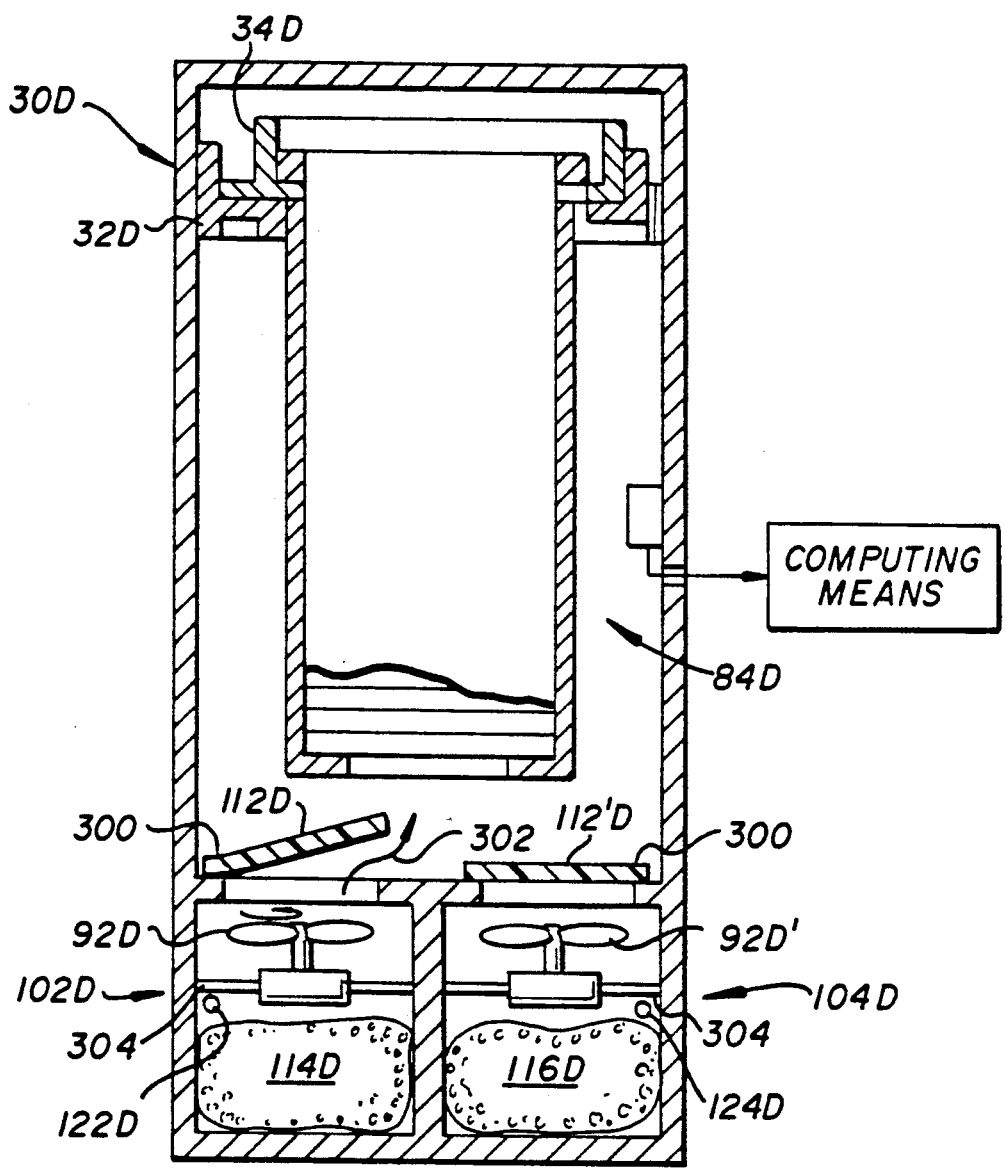
FIG. 7 is an elevational view similar to that of FIG. 2, but illustrating still another alternate embodiment.

The door mechanism for opening and closing air flow from the subcompartments and the fan can be a passive one, that is, one not requiring a motor, FIG. 7. Parts similar to those previously described bear the same reference numeral to which the distinguishing suffix "D" is appended. Thus, track 30D has an upper compartment 84D, two lower subcompartments 102D and 104D and a sponge 114D providing moisture addition and a desiccant 116D to remove moisture as described before. Rail 32D and carrier 34D function as before. However, intermediate compartment 86 is omitted, and two fans 92D and 92D' are used in place of one, each fan being confined to a subcompartment. The door mechanism in this case is a flexible flap 112D and 112D' for each subcompartment. The flaps are secured at edge 300, only, so that the flap is free to lift up when either fan is operating, thus allowing air flow, arrow 302, into upper compartment 84D to add or subtract moisture. Either fan can be a conventional "muffin" fan, that has access ports 304 drawing air from around the sponge, or desiccant. Air returns 122D and 124D are provided as before.

The invention has been described in detail with particular reference to certain preferred embodiments thereof, but it will be understood that variations and modifications can be effected within the spirit and scope of the invention.

What is claimed is:

1. In an analyzer for analyzing body liquids to determine concentration levels of analytes, said analyzer including a plurality of separate, side-by-side conveying means for conveying and supporting a plurality of cartridges containing and supplying test elements for a variety of different assays, means for incubating a test element after a body liquid is deposited onto a test element taken from a cartridge of said conveying means, transfer means for transferring a test element from said conveying means to said incubating means, and means for controlling the relative humidity of said conveying means, said transfer means including means for independently contacting and moving at any one time a test element out of a cartridge in only one of said conveying means;

the improvement wherein said humidity-controlling means comprise separate water-adding means and water-subtracting means for each of said conveying means and control means for each conveying means for controlling the relative humidity of one of said conveying means to be substantially different from the adjacent conveying means, and further including means for preventing substantial intermixing of the atmospheres of said conveying means when said transfer means moves a test element out of said conveying means.

2. An analyzer as defined in claim 1, wherein said control means for each conveying means include a compartment for each of said water-adding means and said water-subtracting means, and door means providing air access to said compartments.

3. An analyzer as defined in claim 2, wherein said door means include closures over each of said compartments.

4. An analyzer as defined in claim 3, wherein said control means comprise a single motor for operating said closures for both said water-adding compartment and said water-subtracting compartment for said conveying means.

5. An analyzer as defined in claim 1, wherein said transfer means include a pusher blade and means for advancing said blade across all of said conveying means.

6. An analyzer as defined in claim 5, wherein said preventing means include movable guides disposed above each of said conveying means, constructed to accommodate said pusher blade and a test element being transferred by said pusher blade, and means for sealing said guides to said conveying means to prevent air intermixing when said conveying means is not supplying a test element to be transferred.

7. An analyzer as defined in claim 1, wherein said preventing means include movable guides disposed above each of said conveying means, constructed to accommodate said transfer means and a test element being transferred by said transfer means, and means for sealing said guides to said conveying means to prevent air intermixing when said conveying means is not supplying a test element to be transferred.

* * * * *